(12) United States Patent
Evers et al.

(10) Patent No.: US 9,023,651 B2
(45) Date of Patent: May 5, 2015

(54) METHOD FOR DETERMINING THE AMOUNT OF MAGNETICALLY LABELED TROPONIN

(75) Inventors: Toon Hendrik Evers, Eindhoven (NL); Wendy Uyen Dittmer, Eindhoven (NL)

(73) Assignee: Koninklijke Philips N.V., Eindhoven (NL)

(\*) Notice: Subject to any disclaimer, the term of this patent is extended or adjusted under 35 U.S.C. 154(b) by 669 days.

(21) Appl. No.: 13/124,407

(22) PCT Filed: Oct. 6, 2009

(86) PCT No.: PCT/IB2009/054372
§ 371 (c)(1),
(2), (4) Date: Apr. 15, 2011

(87) PCT Pub. No.: WO2010/044005
PCT Pub. Date: Apr. 22, 2010

(65) Prior Publication Data
US 2011/0207229 A1 Aug. 25, 2011

(30) Foreign Application Priority Data
Oct. 16, 2008 (EP) .................................... 08166810

(51) Int. Cl.
| | | |
|---|---|---|
| G01N 33/553 | (2006.01) | |
| G01N 33/543 | (2006.01) | |
| B82Y 25/00 | (2011.01) | |
| G01N 27/74 | (2006.01) | |
| G01R 33/09 | (2006.01) | |
| G01R 33/12 | (2006.01) | |
| G01N 35/00 | (2006.01) | |

(52) U.S. Cl.
CPC .......... *G01N 33/54326* (2013.01); *B82Y 25/00* (2013.01); *G01N 27/745* (2013.01); *G01R 33/093* (2013.01); *G01R 33/1269* (2013.01); *G01N 35/0098* (2013.01)

(58) Field of Classification Search
USPC ...................... 436/34, 526; 702/22–23, 26, 32
See application file for complete search history.

(56) References Cited

U.S. PATENT DOCUMENTS

| | | | |
|---|---|---|---|
| 4,368,047 A | | 1/1983 | Andrade |
| 5,885,839 A | | 3/1999 | Lingane |
| 6,551,843 B1 | * | 4/2003 | Rao et al. ..................... 436/526 |
| 6,991,938 B1 | | 1/2006 | Cookson |
| 7,048,890 B2 | * | 5/2006 | Coehoorn et al. ......... 422/82.02 |
| 7,470,540 B2 | * | 12/2008 | Stahler et al. ................... 436/34 |
| 2002/0146835 A1 | | 10/2002 | Modzelewski |
| 2004/0033627 A1 | * | 2/2004 | Aytur et al. .................... 436/526 |
| 2004/0078149 A1 | | 4/2004 | Matzinger |
| 2005/0106758 A1 | * | 5/2005 | Fukumoto et al. ............. 436/526 |

(Continued)

FOREIGN PATENT DOCUMENTS

| | | |
|---|---|---|
| EP | 0667528 A1 | 8/1995 |
| WO | 9322678 A2 | 11/1993 |

(Continued)

*Primary Examiner* — Arlen Soderquist (57) ABSTRACT

The invention relates to a method and a device (100) for determining the amount of a target component (2) in a sample, wherein magnetic particles (2) can bind to a contact surface (4) with kinetics that depend on the sample-amount of the target component. The method comprises at least two washing steps during which magnetic particles (2) are magnetically moved away from the contact surface (4) and corresponding measurements of the remaining amount of magnetic particles (2) at the contact surface (4). The amount of target component in the sample is estimated from at least one of such measurement results. The measurement allows to determine also high concentrations of target component for which the sensor surface (4) is saturated in a steady-state.

9 Claims, 5 Drawing Sheets

(56) References Cited

U.S. PATENT DOCUMENTS

| | | | |
|---|---|---|---|
| 2007/0231926 A1* | 10/2007 | Ikeda | 436/526 |
| 2008/0206892 A1* | 8/2008 | Prins | 436/526 |

FOREIGN PATENT DOCUMENTS

| | | | |
|---|---|---|---|
| WO | 0229411 | A2 | 4/2002 |
| WO | 03049530 | A2 | 6/2003 |
| WO | 2005010542 | A2 | 2/2005 |
| WO | 2005010543 | A1 | 2/2005 |
| WO | 2005111615 | A1 | 11/2005 |
| WO | 2006092036 | A1 | 9/2006 |
| WO | 2006134569 | A2 | 12/2006 |
| WO | 2007132367 | A1 | 11/2007 |
| WO | 2008102218 | A1 | 8/2008 |
| WO | 2009007797 | A1 | 1/2009 |

* cited by examiner

METHOD FOR DETERMINING THE AMOUNT OF MAGNETICALLY LABELED TROPONIN

The invention relates to a method for determining the amount of a target component in a sample, wherein magnetic particles can specifically bind to a contact surface with kinetics that depend on the sample-amount of the target component. Moreover, it relates to a sensor device for executing such a method and an associated computer program.

The U.S. Pat. No. 6,991,938 B1 discloses a method in which the binding of a target substance in a sample to a surface is continuously monitored and correlated to the amount of said target substance in the sample. A problem of this approach is however that the measurements are usually affected by not specifically bound parts of the target substance.

Based on this background it was an object of the present invention to provide means for reliably determining the amount of a target component in a sample.

This objective is achieved by a method, a sensor device, a computer program, and a use as disclosed herein Embodiments are disclosed in the claims.

The method according to the present invention serves for the determination of the amount of a target component in a sample, wherein magnetic particles can specifically bind to a contact surface of a sample chamber which is filled with the sample and wherein said binding takes place with kinetics that depend on the sample-amount of the target component. The amount of target component that is looked for will in the following be briefly called "sample-amount". It is typically measured as a concentration, for example as mass per volume or number of particles per volume. The "target component" can for example comprise biological substances like biomolecules, complexes, cell fractions or cells.

The term "magnetic particle" shall denote a magnetized or magnetizable particle (molecule, complex, nano-particle, micro-particle etc.), for example a superparamagnetic bead. The magnetic particles will often be used as a labels for the target component of interest and chemically bind to them.

The "sample chamber" is typically an empty cavity or a cavity filled with some substance like a gel that may absorb a sample substance; it may be an open cavity, a closed cavity, or a cavity connected to other cavities by fluid connection channels. One part of the wall of the sample chamber is the "contact surface" to which the magnetic particles can specifically bind. Typically, the contact surface will be coated to this end with binding sites (e.g. antibodies) to which the magnetic particles (comprising corresponding antigens) can specifically bind.

The method comprises the following steps:

a) At least two "washing steps", in which a magnetic force is exerted on magnetic particles at the contact surface such that unbound magnetic particles are moved away from the contact surface. While the movement is often directed perpendicularly away from the contact surface, it may also comprise lateral components or even an (at least intermediate) approach to the surface. Appropriate magnetic forces can particularly be executed by generating a magnetic field at the contact surface with a non-zero gradient directed away from the surface. Optionally the magnetic force may be large enough to remove also magnetic particles from the contact surface that are bound but not specifically bound, for example not via a hybridization with specific binding sites but only via weaker forces. The at least two executions of a washing step are separated by (nonzero) time intervals in which no removal of magnetic particles takes place that would be equivalent to a washing.

b) At least two "measurement steps" (each of them associated to another one of the aforementioned washing steps) in which the total amount of magnetic particles at the contact surface is measured during the associated washing step. It should be noted that the "total amount of magnetic particles" comprises specifically bound magnetic particles as well as non-specifically bound and unbound particles. Moreover, the duration of the measurement is independent of the duration of the washing step. A measurement "during" the washing step therefore typically means an instantaneous measurement at any time point in the interval of the washing step, wherein this interval shall by definition also comprise the moment after the active removal of magnetic particles has ended.

It should further be noted that the amount of magnetic particles may be measured magnetically, i.e. via the detection of their magnetism, or via any other suitable method, e.g. the detection of a fluorescent label attached to the magnetic particles.

c) An "estimation step" in which the desired sample-amount of the target component is estimated with the help of the measurement results of the measurement steps.

The described method has the advantage that it allows to determine the amount of the target component in a sample ("sample-amount") from measurements at a contact surface which can be executed during an ongoing process of binding of magnetic particles to the contact surface. This is due to the fact that a magnetic washing of unbound magnetic particles is used, which provides for accurate measurements without an exchange of the sample. The method is fast as it is not necessary to wait until a steady-state is—perhaps very slowly—reached. Moreover, the method provides an increased dynamic range by allowing the determination of high sample-amounts of target component, which lead to a saturation of the binding at the contact surface in a steady-state and which can therefore not reliably be determined in the steady-state. This extension of the upper dynamic limit allows to use larger magnetic particles which in turn improves the lower sensitivity limit.

The magnetic particles are preferably attracted to the contact surface by an attractive magnetic force, for example generated by an appropriately oriented magnetic field gradient, before and/or after a washing step a). In this way the binding of magnetic particles to the contact surface can be accelerated. The strength of the magnetic attraction should be known and/or exactly controlled because it affects the result of a measurement step b) that is made during a non-stationary process.

The measurement of the total amount of magnetic particles at the contact surface in the measurement step b) is preferably made at the end of the associated washing step a) to guarantee that as many unbound magnetic particles as possible are removed from the contact surface.

The washing step a) may be repeated several times, wherein the executions of the washing step are separated by (nonzero) time intervals in which no removal of unbound magnetic particles takes place. Typically, the intermediate time intervals will be used for a magnetic attraction of particles to the contact surface. It should be noted that all remarks and modifications explained above and in the following with respect to "a washing step a)" apply to all repetitions of this step, too.

Though the washing step a) is executed several times in the aforementioned embodiment of the invention, an associated measurement step b) may be executed only twice, i.e. for two single ones of the several washing steps. Preferably, measurement steps b) are however executed for all executions of a washing step a). It should be noted that all remarks and modifications explained above and in the following with respect to "a measurement step b)" apply to all repetitions of this step, too.

The at least two measurement results obtained by the method are preferably exploited by basing the estimation step c) on a plurality of measurement results obtained in different measurement steps b). This can for example be done by estimating a value of the sample-amount of target component from each single measurement and then calculating an appropriate statistical average of these values. In another approach, the plurality of measurement results obtained in different measurement steps can be used to base the estimation of the sample-amount on the change of the measurement results. Thus it is for example possible to calculate the changing rate (slope) of the measurement results, which relates to the kinetics of the binding process and is thus also a reliable indicator for the sample-amount of target component that is looked for.

The estimation of the sample-amount of target component may alternatively be based on a single measurement result obtained in step b), which is a simple and quick method to determine said amount in many situations.

In practice it turns out that the described alternative variants of basing the estimation of the sample-amount of target component on (i) a change of measurement results (i.e. on the kinetics), or (ii) a single measurement result, achieve their highest accuracy for different sample-amounts of target component. When a value for an expected sample-amount of target component is given, this can be exploited to automatically select the most appropriate variant of the method, i.e. to base the estimation on a change of several measurement results, or on a single measurement result, or a combination of both approaches. In assays in which the amount of bound magnetic particles increases with the sample-amount of target component (e.g. in a sandwich assay), the first variant will typically be preferred for high values of the expected sample-amount and the second variant for lower values. An inverse rule holds for e.g. inhibition assays, in which low sample-amounts of target component correspond to high amounts of bound magnetic particles and vice versa. In general one can say that for assays with a fast binding and/or with many bound magnetic particles, a kinetics-based measurement is preferred, while for assays with slow binding and/or few bound magnetic particles, single measurements are favorably used.

The aforementioned expected sample-amount of target component may be given in advance, e.g. via additional information that is available about the sample to be tested. Preferably, the expected sample-amount of target component is however estimated based on the first measurement results obtained during an ongoing assay. Thus the method can be made self-adaptive and automatically select the optimal procedure to deal with samples of a completely unknown contents of target component.

According to another embodiment of the invention, the timing (i.e. start, end) of remaining washing steps and measurement steps is determined based on the measurement results of already executed washing steps and measurement steps. If the first measurement results indicate a high sample-amount of target component, it is for example possible to schedule optimal measurement steps for a determination of the kinetics; if they indicate a low sample-amount of target component, it is possible to optimally schedule a single measurement step for an "endpoint measurement".

A magnetic washing step a) may be such that approximately all (i.e. more than 80%, preferably more than 90%) magnetic particles that are not specifically bound to the contact surface are removed from the contact surface at the end of this step. This can be achieved by applying appropriate magnetic forces that are e.g. high enough and last long enough. A measurement at the end of the washing step will then substantially only include the amount of specifically bound magnetic particles.

Alternatively, a washing step a) may be such that only a fraction of the magnetic particles that are not specifically bound are removed from the contact surface during this step. Such a partial washing can be preferred if a complete washing would take too much time, particularly if a plurality of washing steps shall be executed that allow to determine a change of measurement results.

Depending on the prevailing sample-amount of target component and the binding behavior of the magnetic particles, a saturation of the available bindings at the contact surface may be reached more or less quickly. The timing of the washing steps and the associated measurement steps will preferably take this fact into account to avoid that measurements are made too early (when not enough magnetic particles have bound to the contact surface) or too late (when saturation is already reached at the contact surface). This can for instance be achieved if at least one washing step and the associated measurement step are executed i) after a given lower fraction and/or ii) before a given upper fraction of an expected total time needed to reach the surface saturation. The lower fraction may for example correspond to about 20% and the upper fraction to about 80% of the total time until surface saturation is reached. If there is no estimation available for the expected total time to reach surface saturation in a particular sample, globally valid boundary values can be taken. Thus the timing of the last measurement step ("endpoint measurement") will typically be dependent on the lowest amount of target component that needs to be measured, while earlier "midpoint measurements" are timed to be able to determine the highest amount of target component that needs to be measured.

The estimation step c) exploits the fact that the binding of magnetic particles to the contact surface is governed by physical/chemical laws in dependence on the sample-amount of target component. The measurement results obtained during the intermediate washing steps are therefore reproducibly related to the sample-amount of target component, which allows to infer the sample-amount of target component from the measurements. The mathematical relation between measurement results and sample-amount that is needed for the estimation might be derived from theoretical considerations. Preferably, this relation is however determined from a calibration procedure performed with test samples having different known sample-amounts of target component. The calibration data obtained in this way can be used as a basis for the estimation step. They can for example be provided as a lookup table or as a mathematical formula with fitted parameters.

The invention further relates to a sensor device comprising the following components:

a) A sample chamber in which a sample comprising a target component and magnetic particles can be provided, the sample chamber having a contact surface at which magnetic particles can specifically bind.

b) A magnetic manipulator for exerting a magnetic force on magnetic particles at the contact surface such that unbound magnetic particles are moved away from the contact surface. The magnetic manipulator may for example be realized by an electromagnet that generates a magnetic field gradient at the contact surface.

c) A sensor unit for measuring the total amount of magnetic particles at the contact surface. The sensor unit may for example be an optical, magnetic, mechanical, acoustic, thermal and/or electrical sensor unit. A magnetic sensor unit may particularly comprise a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 or WO 2005/010542 A2, especially a GMR (Giant Magneto Resistance), a TMR (Tunnel Magneto Resistance), or an AMR (Anisotropic Magneto Resistance). An optical sensor unit may particularly be adapted to detect variations in an output light beam that arise from a frustrated total internal reflection due to particles at a sensing surface. Other optical, mechanical, acoustic, and thermal sensor concepts are described in the WO 93/22678, which is incorporated into the present text by reference.

d) A control unit that is connected to the magnetic manipulator and the sensor unit for determining the sample-amount of target component with a method of the kind described above. This means that the control unit is adapted to
   (i) execute at least two washing steps (by making the magnetic manipulator exert a magnetic force on magnetic particles to remove unbound magnetic particles from the contact surface),
   (ii) execute at least two associated measurement steps (by making the sensor unit measure the total amount of magnetic particles at the contact surface during a washing step),
   (iii) estimate the sample-amount of target component with the help of the aforementioned measurement results. The control unit may be realized by dedicated electronic hardware, digital data processing hardware with associated software, or a mixture of both.

The sensor device comprises the components that are needed to execute a method of the kind described above. Therefore, reference is made to the preceding description for more information on the details, advantages and improvements of that device.

The described method will typically be realized with the help of a computing device, e.g. a microprocessor or an FPGA in the control unit of the aforementioned sensor device. Accordingly, the present invention further includes a computer program product which provides the functionality of any of the methods according to the present invention when executed on a computing device.

Further, the present invention includes a data carrier, for example a floppy disk, a hard disk, an EPROM, or a compact disc (CD-ROM), which stores the computer product in a machine readable form and which executes at least one of the methods of the invention when the program stored on the data carrier is executed on a computing device. The data carrier may particularly be suited for storing the program of the computing device mentioned in the previous paragraph.

Nowadays, such software is often offered on the Internet or a company Intranet for download, hence the present invention also includes transmitting the computer product according to the present invention over a local or wide area network.

The invention further relates to the use of the microelectronic device described above for molecular diagnostics, biological sample analysis, or chemical sample analysis, food analysis, and/or forensic analysis. Molecular diagnostics may for example be accomplished with the help of magnetic particles that are directly or indirectly attached to target molecules.

These and other aspects of the invention will be apparent from and elucidated with reference to the embodiment(s) described hereinafter. These embodiments will be described by way of example with the help of the accompanying drawings in which:

Like reference numbers in the Figures refer to identical or similar components.

In many biological assays a large dynamic range (i.e. the range of target component concentrations that can reliably be determined) is desirable. The following examples illustrate a solution how the dynamic range of assays based on magnetic (nano-)particles can be extended.

Magnetic particles or beads can be used as labels for e.g. biological target components (atoms, ions, biomolecules, cells, viruses, or fractions of cells or viruses, tissue extract, etc.) to achieve a rapid, sensitive and easy-to-use molecular diagnostics. In many biosensor devices, the magnetic particles are bound to a contact surface of the sensor device in the presence/absence of the target component, wherein the amount of magnetic particles bound to the surface is dependent upon the concentration of target component in solution.

It is desirable for a sensor device to be able to measure both sensitively and over a large linear dynamic range, i.e. over a large concentration range for which the signal is proportional to the concentration. However, it is often observed that the dynamic range is limited. For magnetic particles larger than 100 nm, the linear range is for example typically limited to about 1-2 orders of magnitude. The dynamic range for a surface detection technique is limited by:
   the lowest density of magnetic particle (label) that can be detected;
   the highest density of magnetic particle (label) that can fit on the surface (assuming that multiple layers of label on the surface do not yield a linear increase in signal).

Using larger magnetic particles is advantageous because this decreases the lowest density of particles that can be detected; however, the highest particle density is thus also decreased because of steric hindrance due to the size of the particles.

As an example, the testing of cardiac troponins requires extremely sensitive measurements in the order of 1 pM, which implies the use of large (300-500 nm diameter) magnetic particles. This comes at the expense of the dynamic range which is low (2 orders), because the signal saturates at high concentrations. In order to fulfill the clinical requirements, it is however necessary to be able to measure at least three decades in concentration.

One way to extend the dynamic range at high concentrations is to perform several determinations at various dilutions of the original sample. Another method is to introduce the samples at different times to change the incubation time (cf. WO/2006/092036). These methods are however cumbersome, error-prone, and require several handling steps.

Another problem that must be kept in mind is that the measurements often also contain a part that is not proportional to the concentration of bound magnetic particle, e.g. aspecific binding of particles to the sensor surface or signal derived from the bulk fluid above the surface.

To address the above problems, a combination of kinetic and endpoint measurements is proposed here that combines the sensitivity of endpoint measurements with the extended dynamic range of kinetic measurements. This can be accomplished by an assay method that makes use of multiple washing steps. This method will in the following be described in more detail.

In sensor devices, washing steps can be carried out by (micro) fluidically replacing the sample fluid containing the target component (analyte) above the sensor area with another fluid that does not contain the target component. This can be complicated and difficult to achieve. Furthermore, it is often impossible to reintroduce the sample fluid to resume the reaction which allows doing a kinetic measurement.

A unique feature of assays that use magnetic particles is the ability to perform a magnetic washing step. The magnetic particles that are near the sensor surface (and thus generating a signal) but have not bound can be simply removed by using a magnet that directs the particles away from the surface. In addition, by tuning the magnetic force, particles that are bound by weak aspecific bonds can also be removed while leaving the specific bonds intact. Such a magnetic washing step can be very fast and completed within a second. Furthermore, there is no need to remove the sample liquid from the sample chamber/sensor area. After the washing step, the signal that is generated by the specifically bound particles can be determined and the reaction can simply be resumed. In this manner, the amount of specifically bound particles can be determined multiple times in a single assay.

FIGS. 1 to 5 illustrate the above concept for a magnetic sensor device 100. The magnetic sensor device 100 comprises a sample chamber 1 in which a liquid sample comprising a target component and magnetic particles 2 can be provided. The sample chamber 1 is at the bottom confined by a contact surface 4 that carries binding sites 3 to which the magnetic particles 2 can specifically bind. The contact surface 4 may be the surface of a substrate, e.g. a silicon substrate in which microelectronic circuits are embedded, or a glass substrate in the case of optical measurements. In general, the magnetic particles 2 are used as labels for some target component one is actually interested in. For simplicity it will in the following be assumed that the magnetic particles 2 are at the same time the target component of interest. It should be noted that in some assays there are magnetic particles that cannot bind to the contact surface 4, for example because they did not previously bind to a target molecule; what will be determined in the following is only the amount of magnetic particles in the sample that can bind.

Below and above the sample chamber 1, an attraction magnet 11 and a repulsion magnet 12, respectively, are disposed. When the attraction magnet 11 is activated, it generates a magnetic field gradient B that attracts magnetic particles 2 to the contact surface 4.

A magnetic sensor unit 10 below the contact surface 4 senses the amount of magnetic particles 2 at the contact surface. This sensing may be achieved by any suitable means, e.g. optically or magnetically. A control unit 13 is connected to the sensor unit 10 and to the magnets 11, 12 to control their activity and to read the sensor signals s. A typical temporal course of the sensor signals s is illustrated in the diagram on the box of the control unit 13.

Figure 1:
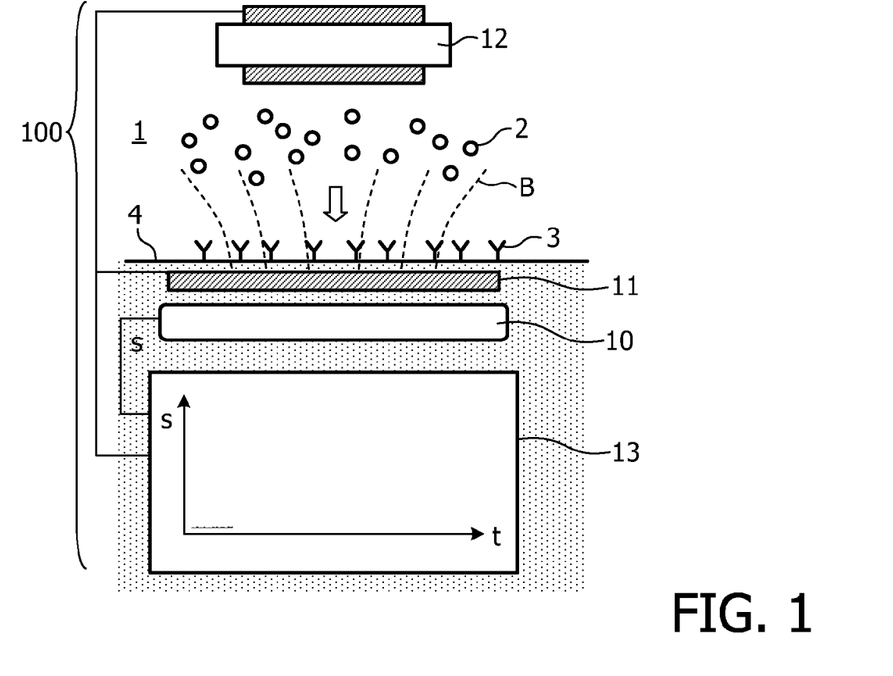
FIGS. 1-5 show consecutive stages of a method according to the present invention.

FIG. 1 shows the situation in which the magnetic particles 2 have just been brought into the sample chamber 1 by filling the latter with the sample. The particles 2 are attracted to the contact surface 4 by the activated attraction magnet 11. As no magnetic particles 2 are yet at the contact surface 4, the corresponding sensor signal s has a low value.

Figure 2:
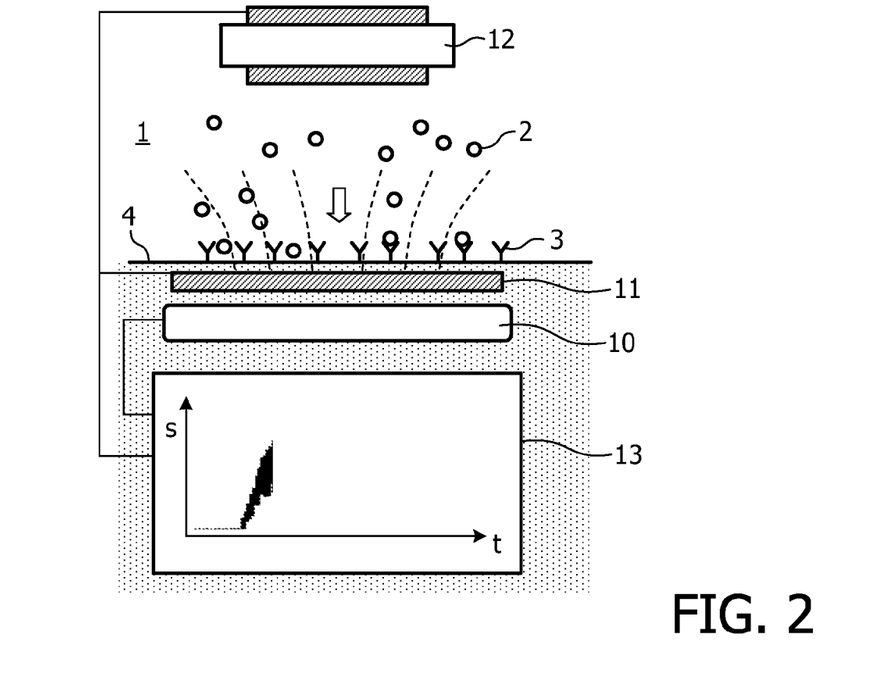

In FIG. 2, first magnetic particles 2 have reached the contact surface 4. The sensor signal s increases accordingly.

Figure 3:
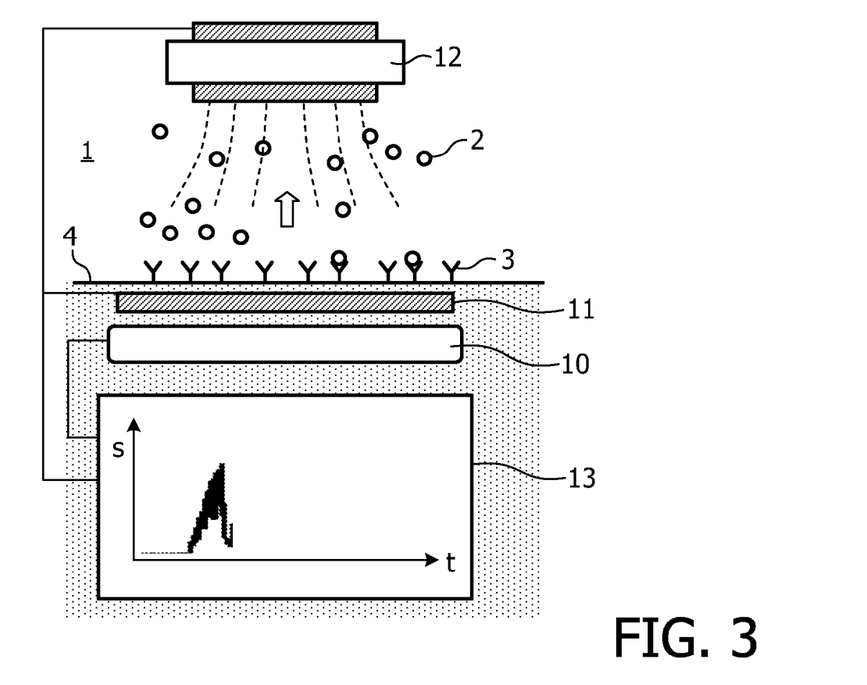

In FIG. 3, the attraction magnet 11 has been switched off and the repulsion magnet 12 has instead been switched on. This generates a magnetic field gradient that pulls magnetic particles 2 away from the contact surface 4. Thus a washing step is realized in which non-specifically bound magnetic particles 2 are removed from the contact surface 4. As a consequence, the sensor signal s drops until it reaches a value that corresponds to the amount of specifically bound magnetic particles. In a measurement step, the control unit 13 can sample and store the corresponding measurement value provided by the sensor 10.

Figure 4:
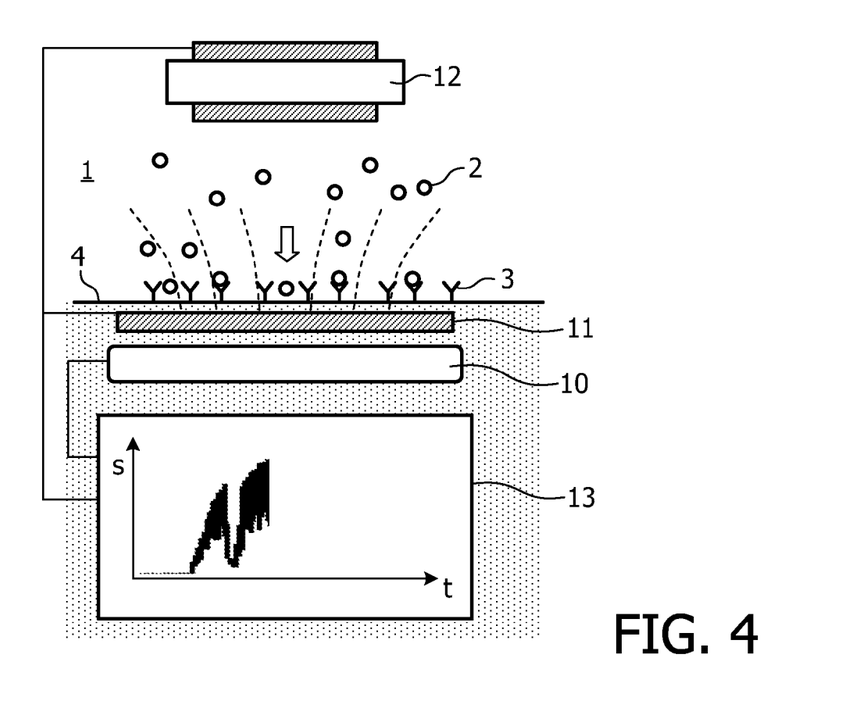

In FIG. 4, the washing step has ended and the attraction magnet 11 has again been activated to pull magnetic particles to the contact surface 4. With the arrival of magnetic particles 2 at the contact surface, the sensor signal s increases accordingly.

Figure 5:
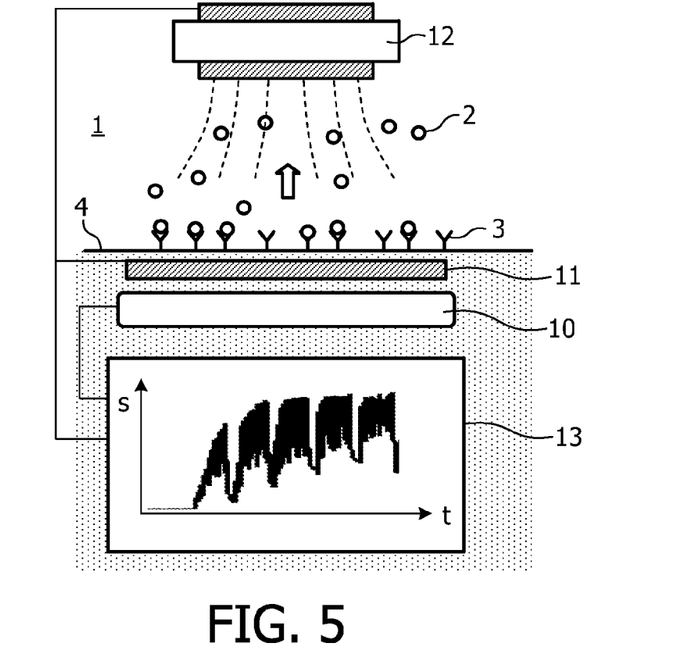

FIG. 5 shows the situation after several repetitions of the magnetic washing and measurement steps (FIG. 3) and the intermediate attraction steps (FIG. 4). The sensors signal s during washing has increased in an oscillating way until it finally approximates a steady-state level. From one or several of the measurement results obtained at the end(s) of the washing steps, the sample-amount of magnetic particles within the sample chamber 1 can be estimated. Different ways to do this will be explained in more detail in the following.

Figure 6:
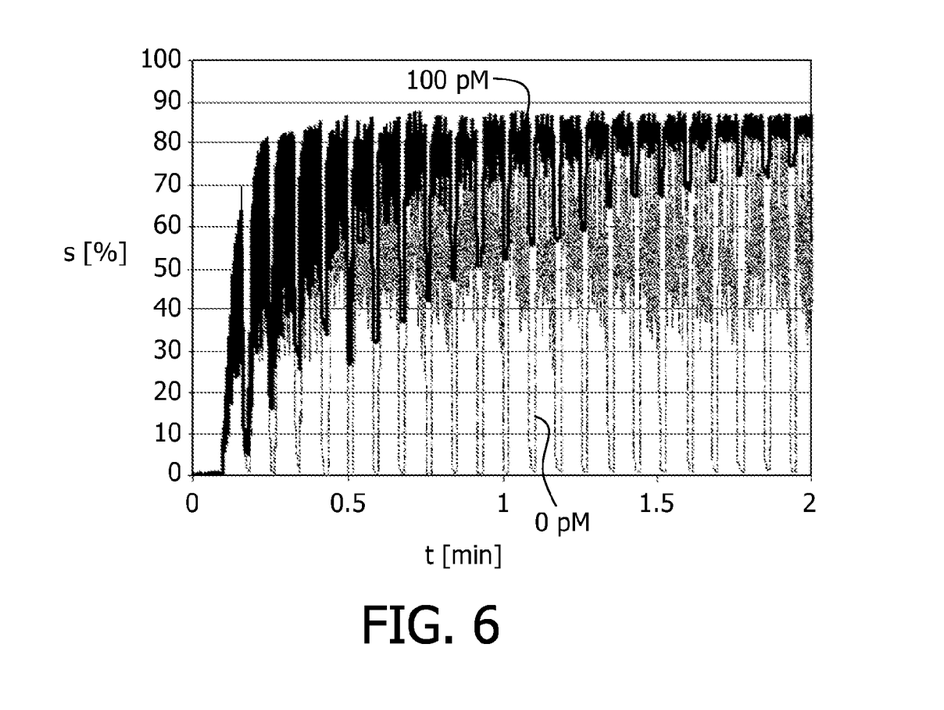
FIG. 6 shows the course of measurement signals over time for two exemplary samples with different amounts of a target component.

In a first embodiment, the attractive actuation that is directed to provide efficient binding of target component labeled with magnetic particles to the contact surface 4 is interrupted by one or more magnetic washing steps, possibly combined with a separate readout step of the sensor signal s. FIG. 6 shows a corresponding diagram with sensor signals s for a concentration of target component of zero (gray curve "0 pM") and 100 pM (solid black curve "100 pM"), respectively. The signal s is here defined in such a way that 0% correspond to a contact surface free of magnetic particles.

In absence of the target component, the sensor signal returns to 0 during the introduced washing steps, because the magnetic particles not linked to a target molecule cannot bind to the contact surface. In presence of 100 pM of the target component, a time-dependent change in the signal can be observed during the washing steps. It is clear from the diagram that during the washing steps many unbound and non-specifically bound particles are removed. Even in the absence of target component the contact surface is quickly saturated by non-bound beads, which are removed during the washing steps.

At each washing step, a "midpoint measurement" can be made and correlated to the (known) sample-amount of target component. This way, a dose-response curve (target component concentration vs. signal) can be plotted for each of these "midpoint measurements".

Figure 7:
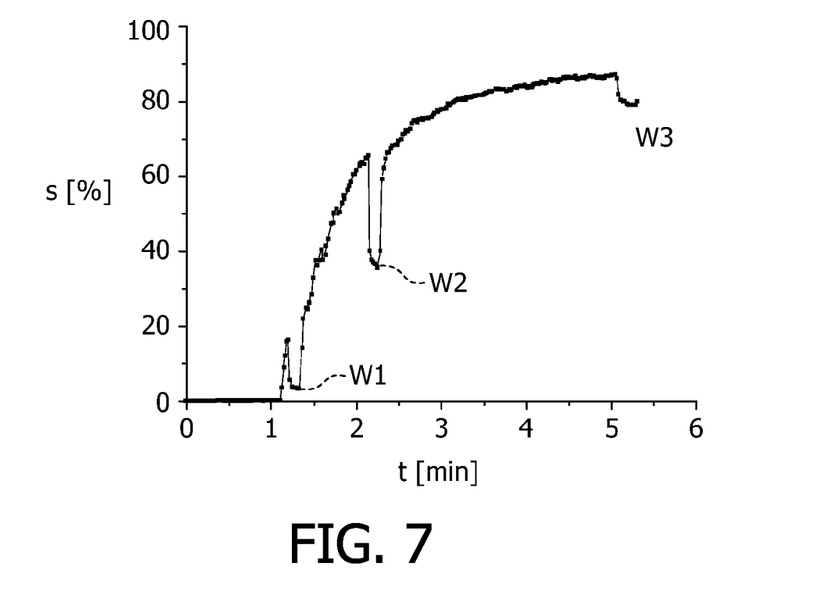
FIG. 7 shows another exemplary course of measurement signals over time with three magnetic washing steps.
Figure 8:
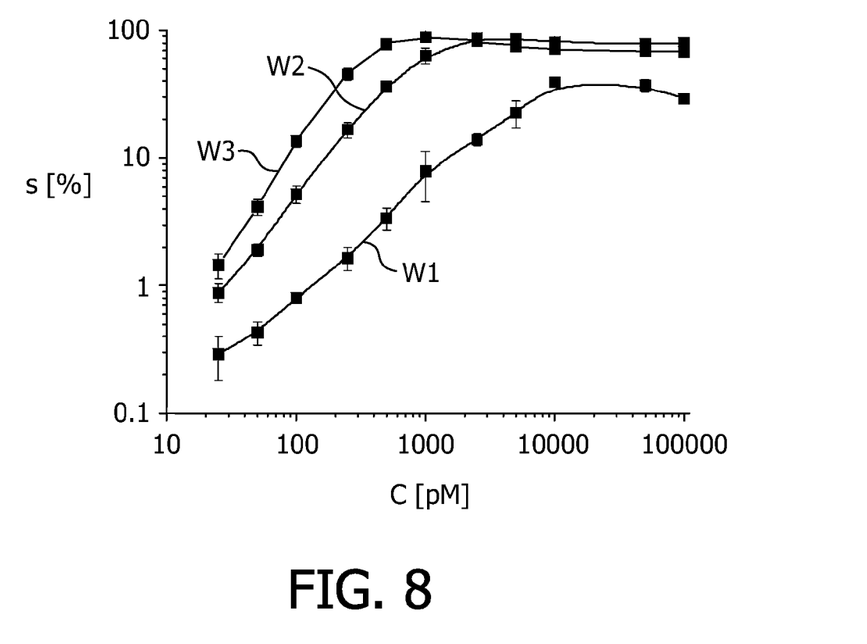
FIG. 8 illustrates experimentally determined dose-response curves that describe the relation between the measurement values during the washing steps of FIG. 7 and the associated sample-amount of target component.

FIGS. 7 and 8 show this in more detail for the exemplary target component troponin. FIG. 7 depicts the measurement curve for a sample with 500 pM troponin and for three washing and measurement steps W1, W2, and W3. FIG. 8 shows the corresponding dose-response curves obtained from a plurality of such measurements for the two midpoint measurements W1, W2 and the endpoint measurement W3 (it should be noted that the term "midpoint measurement" denotes a measurement during a washing step which is followed by a further binding of magnetic particles, while an "endpoint measurement" is just the last measurement of an assay).

For target component concentrations resulting in a slow evolution of the signal, later midpoint measurements can be used. For target component concentrations for which the contact surface 4 is quickly saturated (during the washing steps), earlier midpoint measurements can be used. This results in a much broader dynamic range of the assay.

In a second embodiment similar to the first one, multiple washing steps are introduced during the surface binding. However, instead of using a single midpoint and/or endpoint measurement for a certain sensor response, the slope of the signal changes after the washing step versus time can be used as a measure for the kinetics and thus the amount of target component present in the sample. This method can be easily combined with the described mid/endpoint measurement. For target component concentrations where the signal is saturated at the end of the assay, the assay kinetics/slope can be used, while for the concentrations where the sensor is not saturated, the endpoint measurement can be used, allowing both sensitive measurements and a broad dynamic range of the assay.

Figure 9:
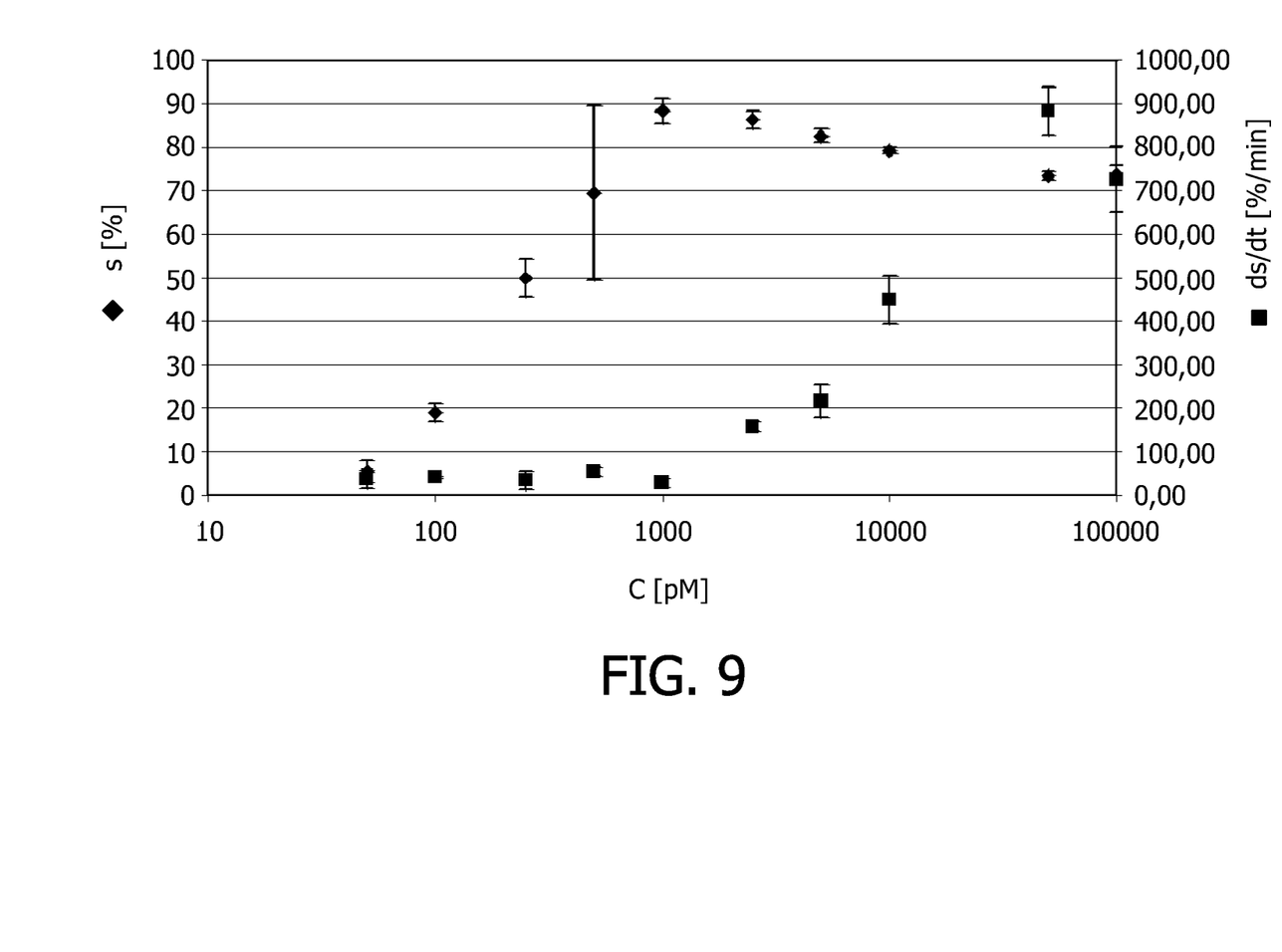
FIG. 9 illustrates different dynamic ranges associated with midpoint based measurements and slope based measurements.

It should be noted that the above mentioned embodiments can be combined. FIG. 9 shows in this respect an example where within one assay both the kinetics (i.e. the slope ds/dt) and the endpoint signal (s) were used as two separate measurements for test samples with different concentrations C of the target component troponin. As can be readily observed, the endpoint measurements (indicated with diamonds and on the left axis) cover linearly a range of lower concentrations C while the slope-based measurements (indicated with squares and on the right axis) cover the range of higher concentrations. Thus the dynamic ranges of each measurement type are entirely different, improving the dynamic range of the whole assay. This is not limited to the combination of kinetic measurements with endpoint measurements, but any combination of one or more kinetic measurements and one or more midpoint measurements and an endpoint measurement is in principle possible.

The distinction which measurement to use for the final readout of the instrument (where a certain signal or slope has to be translated to the unknown quantity of target component present in the sample) can be made automatically by the software running in the control unit 13. For example for the experiments in FIG. 9, if the endpoint measurement yields a signal above a certain value, the kinetic measurement can be used. Or vice versa, if the slope is below a certain value, the endpoint measurement can be used. Such a selection can preferably be made "online" during the begin of an assay with an unknown sample. For example, if the first kinetic or midpoint measurement indicates a high troponin value, the assay could thus be completed in one minute instead of five.

The use of electromagnetic coils to actuate the magnetic particles offers superb control over the manipulation of the magnetic particles. The rate with which the magnetic particles can bind to the surface and hence the rate at which the signal evolves can be controlled by the way the magnetic coils are operated. In other words, the binding rate can be adapted to the specific needs of an individual assay. This in turn means that by means of actuation the dynamic range of the assay can be tuned. This is true for endpoint, midpoint and kinetic measurements. Furthermore, by using different actuation protocols for the different types of measurements WITHIN ONE ASSAY, the dynamic range of each of the measurement types can be tuned (semi) independently. For example, the dynamic ranges of two measurement types can be tailored such that they (slightly) overlap, resulting in a large overall dynamic range of the assay.

While the invention was described above with reference to particular embodiments, various modifications and extensions are possible, for example:

The sensor unit can be any suitable sensor to detect the presence of magnetic particles on or near to a sensor surface, based on any property of the particles, e.g. it can detect via magnetic methods, optical methods (e.g. imaging, fluorescence, chemiluminescence, absorption, scattering, evanescent field techniques, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), combinations thereof, etc.

A magnetic sensor unit can for example be a coil, magneto-resistive sensor, magneto-restrictive sensor, Hall sensor, planar Hall sensor, flux gate sensor, SQUID, magnetic resonance sensor, etc.

Molecular targets often determine the concentration and/or presence of larger moieties, e.g. cells, viruses, or fractions of cells or viruses, tissue extract, etc.

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

The particles serving as labels can be detected directly by the sensing method. As well, the particles can be further processed prior to detection. An example of further processing is that materials are added or that the (bio) chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink jet printing on a substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

With nano-particles are meant particles having at least one dimension ranging between 3 nm and 5000 nm, preferably between 10 nm and 3000 nm, more preferred between 50 nm and 1000 nm.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A method for determining the amount of troponin in a sample over a range from 60 to 100,000 pM, wherein magnetic particles specifically bind to a contact surface of a sample chamber filled with the sample with kinetics that depend on the sample-amount of the troponin, the method comprising the following steps:
   a) a first washing step in which a magnetic force is exerted on the magnetic particles such that the unbound magnetic particles are moved away from the contact surface;
   b) a first measurement step in which the total amount of magnetic particles at the contact surface is measured during the first washing step;
   c) an attracting step for pulling magnetic particles to the contact surface;
   d) a second washing step in which a magnetic force is exerted on the magnetic particles such that the unbound magnetic particles are moved away from the contact surface;
   e) a second measurement in which the total amount of magnetic particles at the contact surface is measured during the second washing step;
   f) estimating the sample-amount of troponin by correlating the result of the first or second measurement with known sample amounts of troponin when the total amount of troponin is below a threshold; and
   g) estimating the sample-amount of troponin by correlating the change between the results of the first and second measurements with known changes in sample amounts of troponin when the total amount of troponin is above a threshold;
   wherein the threshold is 1000 pM.

2. The method according to claim 1, wherein the magnetic particles are attracted to the contact surface by an attractive magnetic force before and/or after the washing steps.

3. The method according to claim 1, wherein the first and second measurement steps are executed at the end of the first and second washing steps, respectively.

4. The method according to claim 1, wherein the timing of washing and measurement steps d) and e) are determined based on the measurement results of already executed washing and measurement steps.

5. The method according to claim 1, wherein magnetic particles that are not specifically bound are removed from the contact surface during the washing steps.

6. The method according to claim 1, wherein only a fraction of the magnetic particles that are not specifically bound are removed from the contact surface during a washing step.

7. The method according to claim 1, wherein at least one washing step and the corresponding measurement step are executed after a given lower fraction and before a given upper fraction of an expected total time needed to reach a saturation of bindings.

8. The method according to claim 1, wherein the estimating is based on calibration data obtained with test samples.

9. A non-transitory computer-readable medium having stored thereon instructions for performing the steps of a method for determining the amount of a target component in a sample, wherein magnetic particles specifically bind to a contact surface of a sample chamber filled with the sample with kinetics that depend on the sample-amount of the target component, the method comprising the steps of claim 1.

* * * * *